United States Patent
O'Neill et al.

(10) Patent No.: US 6,230,036 B1
(45) Date of Patent: *May 8, 2001

(54) SYSTEM FOR RADIOLOGICALLY SCANNING THE SPINE FOR MEASURING BONE DENSITY

(75) Inventors: William O'Neill, Ann Arbor, MI (US); James R. Warne, Washington, PA (US)

(73) Assignee: Hologic, Inc., Waltham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 08/454,716

(22) Filed: May 31, 1995

(Under 37 CFR 1.47)

Related U.S. Application Data

(63) Continuation of application No. 08/295,171, filed on Aug. 22, 1994, now Pat. No. 5,572,998, which is a continuation of application No. 07/947,247, filed on Sep. 18, 1992, now abandoned, which is a continuation-in-part of application No. 07/840,678, filed on Feb. 21, 1992, now abandoned, which is a continuation of application No. 07/713,544, filed on Jun. 7, 1991, now abandoned, which is a continuation of application No. 07/204,513, filed on Jun. 9, 1988, now abandoned, which is a continuation-in-part of application No. 07/050,726, filed on May 15, 1987, now abandoned.

(51) Int. Cl.[7] ..................................................... A61B 6/00
(52) U.S. Cl. ........................... 600/407; 378/55; 378/197; 600/425
(58) Field of Search ................................ 600/425, 436, 600/407; 378/50, 54, 55, 196, 197

(56) References Cited

U.S. PATENT DOCUMENTS

| | | |
|---|---|---|
| 3,803,417 | 4/1974 | Kok . |
| 3,944,830 | 3/1976 | Dissing . |
| 3,988,585 | 10/1976 | O'Neill et al. . |
| 4,012,636 | 3/1977 | Engdahl et al. . |
| 4,107,532 | 8/1978 | MaCovski . |
| 4,144,457 | 3/1979 | Albert . |
| 4,275,305 | 6/1981 | Racz et al. . |
| 4,342,916 | 8/1982 | Jatteau et al. ............................ 378/4 |
| 4,358,856 | 11/1982 | Steivender et al. .................. 378/167 |
| 4,365,343 | 12/1982 | Grady et al. ......................... 378/181 |
| 4,495,645 | 1/1985 | Ohhashi .................................. 382/6 |
| 4,590,378 | 5/1986 | Platz . |
| 4,618,133 | 10/1986 | Siczek . |
| 4,649,560 | 3/1987 | Grady et al. ......................... 378/196 |
| 4,653,083 | 3/1987 | Rossi ................................... 378/196 |
| 4,716,581 | 12/1987 | Barud ................................... 378/198 |
| 4,829,549 | 5/1989 | Vogel et al. ........................... 378/55 |
| 4,856,044 | 8/1989 | Tanguy et al. ....................... 378/193 |
| 4,947,414 | 8/1990 | Stein ..................................... 378/55 |
| 4,986,273 | 1/1991 | O'Neill et al. . |
| 5,165,410 | 11/1992 | Warne et al. . |

FOREIGN PATENT DOCUMENTS

| | | |
|---|---|---|
| 2 238 706 | 2/1974 | (DE) . |
| 24 12 161 | 3/1974 | (DE) . |
| 0 253 742 | 7/1987 | (EP) . |
| 0 265 302 | 9/1987 | (EP) . |
| 86/07531 | 12/1986 | (WO) . |
| 90/10859 | 9/1990 | (WO) . |

OTHER PUBLICATIONS

Rutt, B.K., et al., "High Speed, High–Precision Dual Photon Absorptiometry", Reprint of pester exhibited at meeting at the American Society of Bone and Mineral Research, Jun. 16, 1985, Washington, D.C.

(List continued on next page.)

Primary Examiner—Ruth S. Smith
(74) Attorney, Agent, or Firm—Hamilton, Brook, Smith & Reynolds, P.C.

(57) ABSTRACT

An apparatus employing radiation for measuring bone density in which the bone can be scanned from different angles. The multidirectional scanning is accomplished by rotating the radiation source and detector about the stationary object being irradiated.

31 Claims, 2 Drawing Sheets

OTHER PUBLICATIONS

Pearce, R.B., "DPA Gaining Strength in Bone Scanning Debate", *Diagnostic Imaging* (Jun. 1986).

Norland Corporation advertising brochure for OsteoStatus System pp. 1–8.

A New Dimension in Dual–Photon Absorptiometry Novo Introduces the BMC–Lab 23, Light Years Ahead.

Lunar Radiation Corporation's Users Manual for Lunar DP3 Dual Photon Scanner.

Brochure, "Osteotek Bone Densitometry", Medical & Scientific Enterprises, Inc.

Sartoris, D.J. et al., "Trabecular Bone Density in the Proximal Femur: Quantitative CT Assessment", *Radiology*, 160:707–712 (1986).

Mazess, R.B., et al., "Spine and Femur Density Using Dual–Photon Absorptiometry in US White Women", *Bone and Mineral*, 2:211–219 (1987).

Weissberger, M.A., et al., "Computed Tomography Scanning for the Measurement of Bone Mineral in the Human Spine", *Journal of Computer Assisted Tomography*, 2:253–262 (Jul. 1978).

Genant, H., "Assessing Osteoporosis: CT's Quantitative Advantage", *Diagnostic Imaging*, (Aug. 1985).

Wahner et al. "Assement of Bone Mineral. Part 1" *J. Nuclear Medicine 25(10) :1134–1141 (1984)*.

Mazess, "Dual Photon Absorptiometry and Osteoporosis—Absorptiometric Instrumentation" Meeting publication.

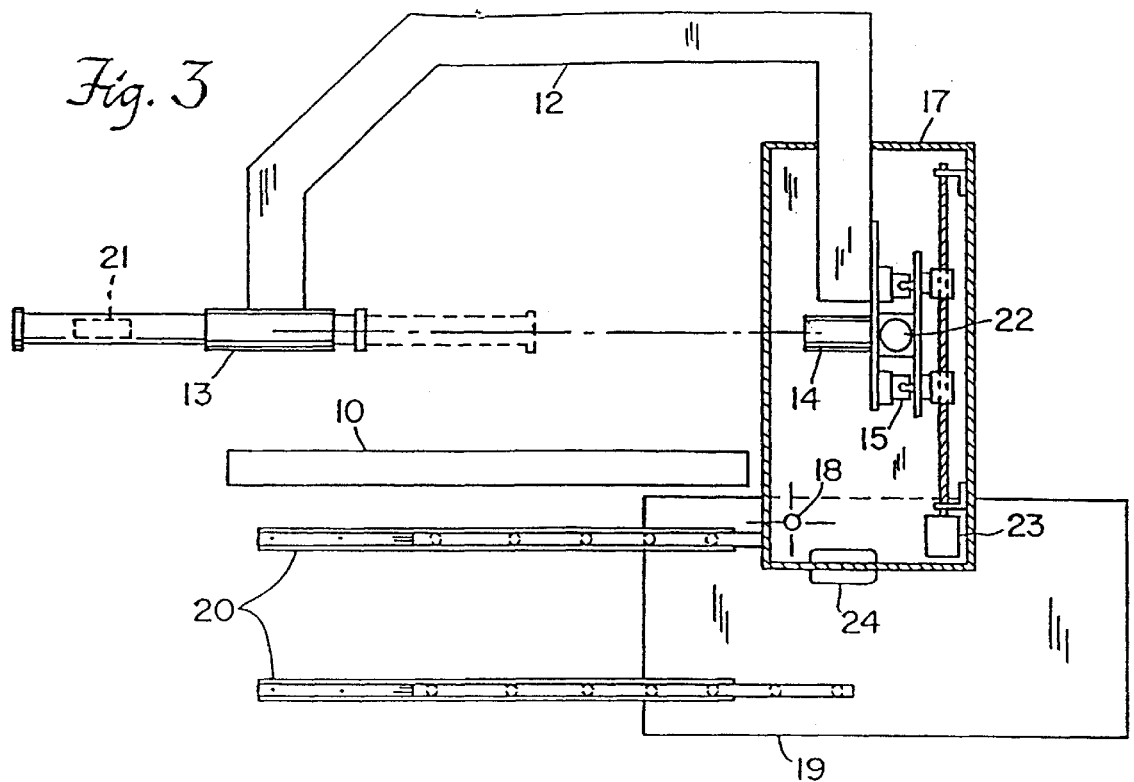
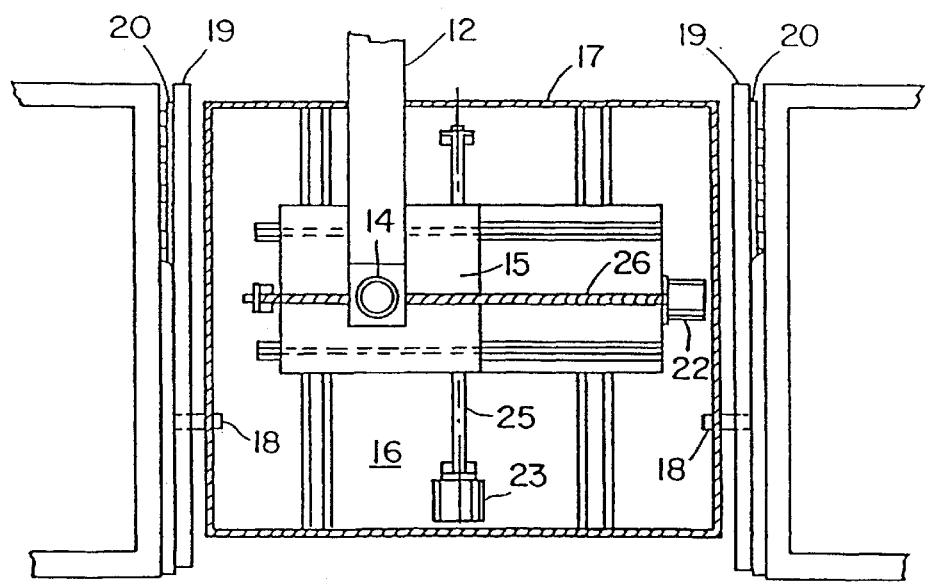

SYSTEM FOR RADIOLOGICALLY SCANNING THE SPINE FOR MEASURING BONE DENSITY

RELATED APPLICATIONS

This application is a Continuation of U.S. Ser. No. 08/295,171 filed Aug. 22, 1994 (now U.S. Pat. No. 5,572,998) which is a Continuation of U.S. Ser. No. 07/947,247 filed Sep. 18, 1992 (now abandoned) which is a Continuation-in-Part of U.S. Ser. No. 07/840,678 filed Feb. 21, 1992 (now abandoned) which is a Continuation of U.S. Ser. No. 07/713,544 filed Jun. 7, 1991 (now abandoned) which is a Continuation of U.S. Ser. No. 07/204,513 filed Jun. 9, 1988 (now abandoned) which is a Continuation-in-Part of U.S. Ser. No. 07/050,726 (now abandoned) filed May 15, 1987.

BACKGROUND OF THE INVENTION

This invention relates to radiologic measuring devices, and more particularly, to the use of radiation in measuring bone structure.

The diagnostic use of radiation in evaluating bone structure has recently been applied in assessing bone demineralization that occurs with advancing age. Bone mineral is lost from all parts of the skeleton, and at a linear rate from the lumbar spine, starting at about 35 years of age. The resultant demineralization results in a high risk of fractures with an increased associated mortality and morbidity. In evaluation of the spine, there is a very good correlation between dual photon densitometry measurements of bone density and fracture resistance in excised vertebrae subjected to compression testing. It is also important to evaluate mineral loss in the hip, as appendicular losses often match or exceed spine loss in patients over 70.

Dual photon absorptiometry enables non-invasive quantitative analysis of bone mineral in regions of the body that were previously inaccessible using single photon absorptiometry.,The use of two photon energies minimizes errors that result from irregular body contour and soft tissue inhomogeneities. Essentially, two photon energies are necessary to allow discrimination of two substances of a given system. In this case between bone mineral and soft tissue. The most commonly used photon energies in dual photon scanning are 44 and 100 KeV. The measurements of the attenuation of this radiation as it passes through the body yields the bone mineral density.

SUMMARY OF THE INVENTION

The present invention involves the multidirectional measurement of human bone densities for diagnostic purposes. A radiation source, and a detector used for measuring the radiation transmitted through the object being measured, are rigidly aligned by a bracket or arm. This detector is mounted in a telescoping mechanism to permit control over the source/detector distance. The arm and the attached source and detector, are mounted on an "x-y" table that permits scanning of objects over a predetermined planar area. This apparatus is mounted so that the source, detector, and scanning mechanism can be rotated to view a stationary object from different angles.

In a preferred embodiment of the invention, the pivot axis about which the arm rotates is displaceable so that the source will clear the table upon rotation. The rotating apparatus may be mounted in a drawer with guides or rails that telescope out to support the system during rotation. The rotating elements are weighted so that very little pressure is necessary to rotate the system. The weight is distributed so that if the mechanism is stopped at any point during rotation, it will at most slowly accelerate under its own weight. If the center of gravity of the rotating mechanism is approximately along the pivot axis, this condition will be met. One weight is placed in the detector to vertically adjust the center of gravity. A second weight is placed adjacent the scanning assembly to horizontally adjust the center of gravity.

BRIEF DESCRIPTION OF THE DRAWINGS

FIG. 3 is a side view of the apparatus rotated to the lateral position.

FIG. 4 is a top view of the saddle and drawer assembly.

DETAILED DESCRIPTION OF THE INVENTION

Existing scanner assemblies used in bone densitometry generally permit unidirectional scanning of patients only. To obtain lateral or side views, for example, the patient must be turned. This movement of the patient is often difficult or impossible depending upon their physical condition.

Figure 1:
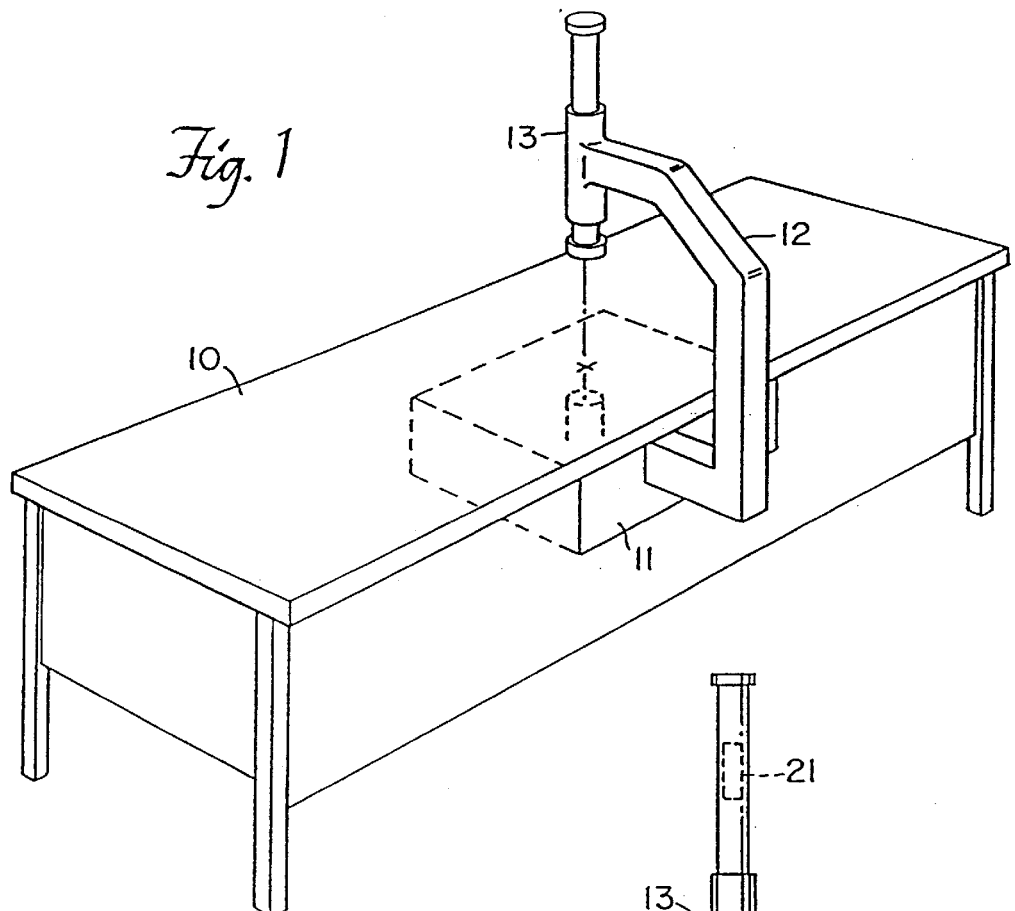
FIG. 1 is a perspective view of the bone densitometer.
Figure 2:
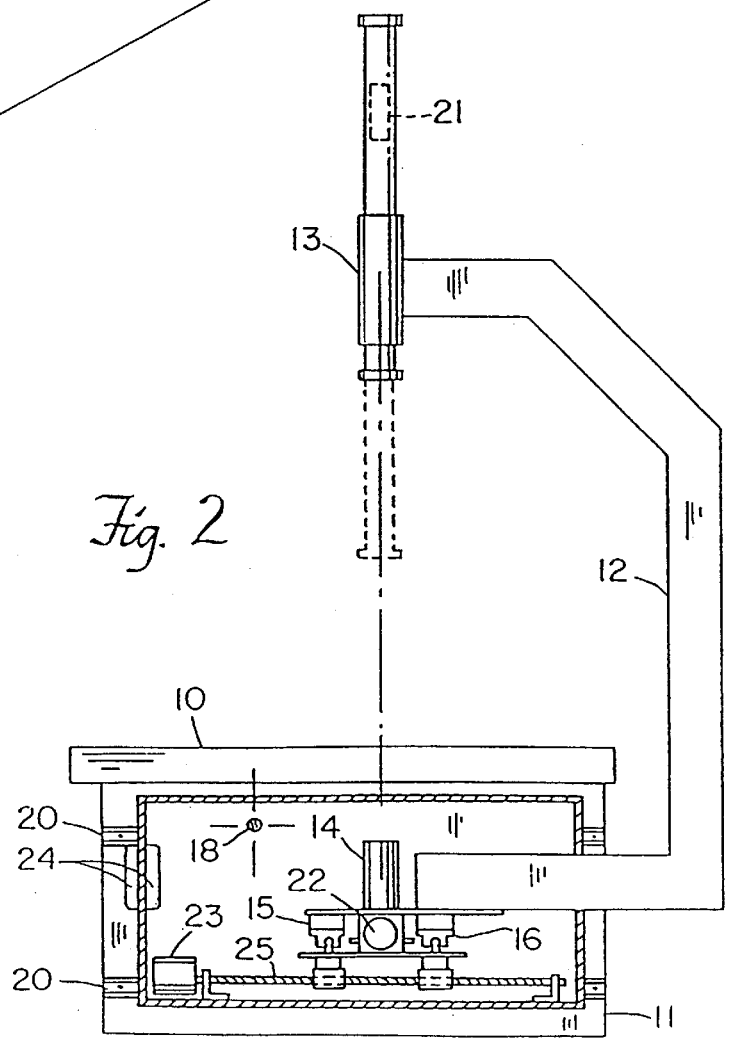
FIG. 2 is a side view of the radiation source and detector in the interior position.

A dual photon bone densitometer used in diagnosing osteoporosis is illustrated generally in FIG. 1. A table 10 on which the patient lies has a drawer assembly 11 which is pulled out from under the table on the side from which a bracket 12 protrudes. The bracket 12 extends in a "C" shape from the drawer assembly 11 to a detecting apparatus 13. FIG. 2 shows, in a cross-sectional view, the relationship between the detector 13 and the contents of the drawer assembly 11.

A radiation source 14 is mounted on a moveable platform 15. The source 14 is rigidly aligned with the detector 13 by bracket 12 to insure that radiation emitted from the source is received by the detector regardless of the angle to which the source-detector axis is rotated. The entire rotatable apparatus is mounted on a tray or "saddle"' 17. The saddle 17 is rotatably mounted onto the assembly plates 19. The plates 19 in one embodiment constitute the side walls of a drawer which compactly houses the source and scanning apparatus.

To rotate the apparatus from the anterior position shown in FIG. 2 to the lateral position shown in FIG. 3, the following steps must be taken. The user releases a locking mechanism and pulls the arm horizontally to one side of the table so that the saddle 17 and plates 19 slide the source from under the center of the table to avoid contact with the table during rotation. In one embodiment of the invention the source is approximately one inch below the table during anterior scanning and thus cannot be rotated without lateral movement. Source proximity to the table is desirable, as the source and detector are preferably as close to one another as possible to yield the best possible image. The drawer assembly plates 19 telescope out along the glides 20 until the pivot point 18 is astride the table 10. The plates 19 are then locked in position by a locking mechanism (not shown). The arm 12 and the attached source and saddle assembly 17 are rotated manually by the user about the axis 18 to the desired position. Note that the pivot axis location must be chosen so that the source and scanning apparatus are rotated into a position just above the plane of the table. This insures that objects positioned on the table can be fully scanned laterally. The pivot location also affects the adjustment of the center of gravity as discussed below. In an alternative embodiment of the invention, the lateral movement of the drawer assembly and/or the rotation may be automatically controlled by adding the necessary motor and control systems.

FIGS. 2 and 3 also illustrate the presence of weights 21 and 24. After initial assembly of the apparatus, the center of gravity of the rotating elements must be adjusted to assure ease of manual rotation. In a preferred embodiment of the invention, the center of gravity of the rotating elements is located along the pivot axis 18. When the center of gravity is so situated the rotating elements will not accelerate under their own weight when the bracket 12 is rotated to any chosen angle, stopped and released.

FIG. 4 shows a top view of the drawer assembly 11 and illustrates the location of the pivot axis 18, the glides 20 for displacement of the plates 19, and the tracks 26 on which the platform 15 rides. The platform 15, as well as the attached source 14, bracket 12, and detector 13, are moved in a plane perpendicular to the source-detector axis. The driving mechanism for the scanning motion is a so-called "x-y" table 16. The scanning mechanism is comprised of threaded bars, one running along the longitudinal or "y" axis 26 of the table, the second 25 running perpendicular to the first across the width or "x" axis of the table. The platform 15 has threaded housings which receive, and are driven by, the two threaded bars. The threaded "x" bar 25 is rotated by a motor 23 and the threaded "y" bar 26 is rotated by the motor 22. When the scanning assembly is rotated along with the source and detector, this insures full scanning capability at any angle. In a preferred embodiment of the invention, the scanning mechanism is controlled automatically feeding by the scanning rate and the size of the area to be scanned into a computer, which then triggers the radiation source and coordinates the desired scan.

During initial rotation of the system from the vertical position, the weight of the saddle and enclosed elements controls the balancing of the bracket 12 and the attached components. The weights 24 are added to the front wall of the saddle to adjust the center of gravity in the horizontal plane. The weight 21 is added to the detector system to adjust the center of gravity in the vertical plane. As the system is rotated through larger angles from the vertical (e.g. 45°–90°), the correct weighting of the bracket and detector by weight 21 becomes more important to maintain ease of manual rotation.

By rotating the detector arm, scanning of the lumbar spine in both the anterior and lateral projections is now possible without repositioning the patient. The patient remaining in the supine position for both the lateral and anterior-posterior projection maintains the correct alignment of both projections, permits direct correlation of the two studies, and anatomically is diagnostically correct.

Performing the lateral image as the first study may enable the physician to observe extra-osseous calcification in tissue overlying the lumbar spine. In the anterior-posterior projections, such extra-osseous calcification cannot be distinguished from bone, and could therefore interfere with accurate bone density measurements in that projection. The bone being studied may be examined in real time by amplifying the signal output from the detector and displaying it on a C-T screen.

While the invention has been particularly shown and described with reference to preferred embodiments thereof, it will be understood by those skilled in the art that various changes in form and details may be made without departing from the spirit and scope of the. invention as defined in the appended claims.

We claim:

1. An apparatus for measuring bone density in the spinal column of a subject comprising:

a support upon which the subject can be positioned with the spinal column extending along an axis of the support such that the subject remains in one position at a first angle scan and at a second angle scan;

a radiation source and a detector positioned to receive radiation emitted from the source to measure intensity of radiation transmitted through the subject at two energies, the position of the radiation source and detector at one of the first or second angles providing one of an anterior or posterior view of the spinal column such that the radiation source directs radiation through the support to the detector and the other angle scan providing a lateral view of the spinal column, the source and detector being positioned above a plane in which the support is positioned to obtain the lateral view;

a member attached to the source and detector to provide rigid alignment of the source and the detector;

a first driving mechanism causing relative displacement between said support and said aligned source and detector in a direction along the support axis to detect radiation at the two energies with the detector and measure bone density of the spinal column of the subject;

a second driving mechanism causing relative displacement between said support and said source and detector in a direction perpendicular to the support surface axis; and a structure on which the member, source and detector are moveably mounted to provide rotation of the source and detector from the first angle to the second angle of the member relative to the support which is different from the first angle.

2. The apparatus of claim 1 wherein the member translates relative to the support such that the source and detector are displaced to one side of the region of the spinal column.

3. The apparatus of claim 1 further comprising:

a tray mounted relative to the support to provide rotation about a pivot axis, the source being positioned under the support and the pivot axis within the tray; and telescoping rails that guide movement of the tray in a direction perpendicular to the pivot axis.

4. An apparatus for measuring bone density in the spinal column of a subject comprising:

a support surface upon which the subject can be positioned with the spinal column extending along an axis of the support surface, the support surface being stationary during scanning of the subject such that the subject remains in one position at a first angle scan and at a second angle scan;

a radiation source and a detector positioned to receive radiation emitted from the source and transmitted through the subject at two energies, the first angle scan providing one of an anterior or posterior view of the spinal column such that the source directs radiation through the support to the detector and the second angle scan providing a lateral view of the spinal column, the source and detector being positioned above a plane in which the support is positioned to obtain the lateral view;

a C-shaped member attached to the source and detector to provide rigid alignment of the source and the detector;

a drive mechanism displacing the C-shaped member, source and detector in a direction along the support surface axis to scan a region of the spinal column at the first angle such that the detector detects radiation at the two energies to measure bone density in the spinal column; and a translating support on which the C-shaped member, source and detector are mounted, the C-shaped member, source and detector being movably mounted to provide for rotation of the source and detector to the second angle such that the alignment axis extends laterally through the scanned spinal region at the second angle different from the first angle.

5. The apparatus of claim 4 wherein the translating support translates such that the source and detector are displaced relative to the support surface to one side of the region of the spinal column.

6. The apparatus of claim 4 further comprising:
a tray mounted relative to the support to provide rotation about a pivot axis, the source being suspended along the pivot axis within the tray; and
telescoping rails for displacing the tray in a direction perpendicular to the pivot axis.

7. An apparatus for radiologically scanning a bodily region of a subject comprising:
a support surface upon which the subject can be positioned with the spinal column extending along an axis of the support surface during scanning of the subject such that a subject remains in one position at the first angle scan and at a second angle scan;
a radiation source and a detector positioned to receive radiation emitted from the source and transmitted through the subject at two energies, the first angle scan providing one of an anterior or posterior view of the spinal column such that the source directs radiation through the support to the detector and the second angle scan providing a lateral view of the spinal column, the source and detector being positioned above a plane in which the support is positioned to obtain the lateral view;
a C-shaped member attached to the source and detector to provide rigid alignment of the source and the detector;
a drive mechanism displacing the C-shaped member, source and detector along the axis of the support surface to scan a region of the body at the first angle; and
a translating support on which the C-shaped member, source and detector are mounted to rotate to the second angle such that radiation is transmitted through a region of the body at the second angle different from the first angle, the C-shaped member source and detector moving relative to the support surface to position the source and detector at the second angle.

8. The apparatus of claim 7 further comprising an adjustment mechanism to adjust the distance between the support and the detector.

9. The apparatus of claims 7 wherein the C-shaped member, source and detector rotates such that scanning at the first angle comprises scanning in an anterior or posterior direction and scanning at the second angle comprises scanning in a lateral of a region of the body.

10. The apparatus of claim 7 wherein the translating support translates such that the source and detector are displaced to one side of the region of the body.

11. The apparatus of claim 7 wherein the translating support comprises a tray which rotates about a pivot axis, the source being suspended along the pivot axis within the tray.

12. The apparatus of claim 11 further comprising telescoping rails along which the tray is displaced in a direction perpendicular to the pivot axis.

13. The apparatus of claim 11 further comprising a balance element for balancing the C-shaped member, source and detector during rotation.

14. An apparatus for radiologically scanning a bodily region of a subject comprising:
a support surface upon which the subject can be positioned with the spinal column extending along an axis of the support surface;
a radiation source and a detector that detects radiation emitted from the source and transmitted through the subject at two energies;
a telescoping mechanism to adjust a distance between the source and the detector;
a C-shaped member attached to the source and detector to provide rigid alignment of the source and the detector;
a drive mechanism displacing the C-shaped member, source and detector to scan a region of the body at a first angle along the axis of the support surface; and
a translating support on which the C-shaped member, source and detector are movably mounted to provide a horizontal axis about which the C-shaped member, source and detector rotate, the translating support being positioned in a horizontal plane, and the C-shaped member, source and detector being mounted to provide rotation about the horizontal axis to a second angle such that radiation is transmitted through the region of the body at a second angle different from the first angle, the drive mechanism displacing the C-shaped member, source and detector to scan the region of the body at the second angle along the axis of the support surface.

15. The apparatus of claim 14 wherein the detector measures radiation from the source and generates signals processed to provide bone density of the scanned region of the body.

16. The apparatus of claim 14 wherein the region of the body comprises bone such that a computer computes mineral content of the bone.

17. The apparatus of claim 14 wherein the support rotates the C-shaped member, source and detector to permit scanning at the first angle from an anterior-position projection and scanning at the second angle from a lateral projection of the region of the body.

18. The apparatus of claim 14 wherein the support translates such that the source and detector are displaced to one side of the region of the body.

19. The apparatus of claim 14 wherein the translating support comprises a tray having a pivot axis, the source being suspended along the pivot axis within the tray.

20. The apparatus of claim 19 further comprises telescoping rails for displacing the tray in a direction perpendicular to the pivot axis.

21. The apparatus of claim 19 further comprising a balance element for balancing the C-shaped member, source and detector during rotation.

22. The apparatus of claim 19 further comprising a display on which an image of the bodily region can be displayed.

23. A dual energy bone densitometer for measuring bone mineral density in the spine of a person comprising:
a horizontal support surface adapted for supporting a person in a supine position with the spine extending in a given direction along an axis of the support surface such that the subject remains in one position at a first angle scan and at a second angle scan;
a C-shaped member positioned generally in a vertical plane perpendicular to said direction of the axis of the support surface, the first angle scan providing one of an anterior or posterior view of the spinal column such that the source directs radiation through the support to the detector and the second angle scan providing a lateral view of the spinal column, the source and detector being positioned above a plane in which the support is positioned to obtain the lateral view;

a radiation source and a detector mounted on said C-shaped member in spaced-apart relationship and in rigid alignment with the vertical plane during scanning of the spine, the detector being aligned with the source and measuring dual energy radiation transmitted through the spine between the source and detector, the C-shaped member having a first position establishing the first angle of the aligned source and detector relative to the support surface;

a drive mechanism that actuates a scan of the C-shaped member in the direction along the support surface axis while dual energy radiation passing through the region of the spine of the patient is detected to produce a first dual energy scan of the spine measuring bone mineral density of the spine at the first angle;

the C-shaped member, with said radiation source and detector thereon, being mounted to provide rotation about a horizontal axis to a second position to align the source and detector at the second angle in the vertical plane; and said C-shaped member at the second angle, with said radiation source and detector mounted thereon, being actuated by the drive mechanism to scan the C-shaped member in a direction along the support surface axis while dual energy radiation passing through the region of the spine is measured by the detector, to produce a second dual energy scan of the spine of the supine person to measure bone mineral density of the spine at the second angle.

24. The dual energy bone densitometer of claim 23 further comprising an adjustment mechanism to cause relative displacement between the detector and the support surface.

25. An apparatus for measuring bone density in the spinal column of a subject comprising:

a support upon which the subject is adapted to be positioned with the spinal column extending along an axis of the support such that the subject remains in one position at a first angle scan and at a second angle scan;

a dual energy radiation source and a detector positioned to receive radiation emitted from the source to measure intensity of radiation transmitted through the subject at two energies, the position of the radiation source and detector at one of the first or second angles providing one of an anterior or posterior view of the spinal column such that the source directs radiation through the support to the detector and the other angle scan providing a lateral view of the spinal column, the source and detector being positioned above a plane in which the support is positioned;

a member attached to the source and detector to provide rigid alignment of the source and the detector;

a driving mechanism causing relative displacement between said support and said source and detector in a direction along the support axis to scan a region of the spinal column at a first angle of the member relative to the support; and a structure on which the member, source and detector are moveably mounted to provide rotation of the source and detector to a second angle of the member relative to the support which is different from the first angle, to scan a region of the spinal column at the second angle to measure intensity of radiation transmitted through a region of the spinal column at the second angle.

26. The apparatus of claim 25 wherein the member translates relative to the support such that the source and detector are displaced to one side of the region of the spinal column.

27. The apparatus of claim 25 further comprising:

a tray mounted relative to the support to provide rotation about a pivot axis, the source being positioned under the support and the pivot axis within the tray; and telescoping rails that guide movement of the tray in a direction perpendicular to the pivot axis.

28. An apparatus for measuring bone density in a spinal column of a subject comprising:

a support surface upon which the subject can be positioned with the spinal column extending along an axis of the support surface, the support surface being stationary during scanning of the subject such that the subject remains in one position at a first angle scan and at a second angle scan;

a dual energy radiation source and a detector positioned to receive radiation emitted from the source and transmitted through the subject at two energies, the position of the radiation source and detector at one of the first or second angles providing one of an anterior or posterior view of the spinal column such that the source directs radiation through the support to the detector and the other angle scan providing a lateral view of the spinal column, the source and detector being positioned above a plane in which the support is positioned;

a C-shaped member attached to the source and detector to provide rigid alignment of the source and the detector;

a drive mechanism displacing the C-shaped member, source and detector in a direction along the support axis to scan a region of the spinal column at the first angle; and a translating support on which the C-shaped member, source and detector are mounted, the C-shaped member, source and detector being movably mounted to provide for rotation of the source and detector to the second angle such that the alignment axis extends through the scanned spinal region at a second angle different from the first angle, the drive mechanism displacing the C-shaped member, source and detector to scan a region of the spinal column at the second angle.

29. The apparatus of claim 28 wherein the subject remains in one position at the first angle scan and at the second angle scan, the first angle scan providing one of an anterior or posterior view of the spinal column such that the source directs radiation through the support to the detector and the second angle scan providing a lateral view of the spinal column, the source and detector being positioned above a plane in which the support is positioned.

30. The apparatus of claim 29 further comprising:

a tray mounted relative to the support to provide rotation about a pivot axis, the source being suspended along the pivot axis within the tray; and telescoping rails for displacing the tray in a direction perpendicular to the pivot axis.

31. The apparatus of claim 28 wherein the translating support translates such that the source and detector are displaced relative to the support surface to one side of the region of the spinal column.

* * * * *